United States Patent
Meritet et al.

(10) Patent No.: US 7,244,818 B2
(45) Date of Patent: Jul. 17, 2007

(54) INTERFERON ALPHA RESPONSIVE PROTEIN

(75) Inventors: Jean-François Meritet, Paris (FR); Michel Dron, Bourg la Reine (FR); Michael Gerard Tovey, Paris (FR)

(73) Assignee: Pharma Pacific Pty. Ltd., Victoria (AU)

( * ) Notice: Subject to any disclaimer, the term of this patent is extended or adjusted under 35 U.S.C. 154(b) by 414 days.

(21) Appl. No.: 10/149,992

(22) PCT Filed: Dec. 13, 2000

(86) PCT No.: PCT/GB00/04791

§ 371 (c)(1),
(2), (4) Date: Nov. 6, 2002

(87) PCT Pub. No.: WO01/42301

PCT Pub. Date: Jun. 14, 2001

(65) Prior Publication Data

US 2005/0176094 A1 Aug. 11, 2005

(30) Foreign Application Priority Data

Dec. 13, 1999 (GB) ................... 9929453.0
Feb. 11, 2000 (GB) ................... 0003274.8

(51) Int. Cl.
*C07K 14/52* (2006.01)
*A61K 38/21* (2006.01)
*A61K 38/00* (2006.01)

(52) U.S. Cl. .................... 530/350; 424/278.1
(58) Field of Classification Search ............. 530/350; 424/278.1; 435/235.1; 414/278.1
See application file for complete search history.

(56) References Cited

FOREIGN PATENT DOCUMENTS

EP    1 033 401 A2    9/2000

OTHER PUBLICATIONS

Turner et al. (1997) C-terminal deletion mutant of pokeweed antiviral protein inhibits viral infection but does not depurinate host ribosomes. Proc. Natl. Acad. Sci. U S A. vol. 94, No. 8, pp. 3866-3871.*
Virus-Wikipedia (2006) Virus, http://en.wikipedia.org/wiki/Virus, pp. 1-10.*
Eid, P., et al., "Oromucosal Interferon Therapy: Pharmacokinetics and Pharmacodynamics," *Journal of Interferon and Cytokine Research*, 1999, pp. 157-169, vol. 19(2).
Tovey, M., et al., "Mucosal Cytokine Therapy: Marked Antiviral and Antitumor Activity," *Journal of Interferon and Cytokine Research*, 1999, pp. 911-921, vol. 19(8).
Nucleotide and Protein Database Report for Accession No. AA039276, Aug. 31, 1996 (XP-002166661).
Nucleotide and Protein Database Report for Accession AI978890, Sep. 1, 1999 (XP-002166662).
Nucleotide and Protein Database Report for Accession AI698747, Jun. 4, 1999 (XP-002166663).
Nucleotide and Protein Database Report for Accession AI310324, Dec. 14, 1998 (XP-002166664).
Nucleotide and Protein Database Report for Accession AA126974, Dec. 5, 1996 (XP-002166665).
Nucleotide and Protein Database Report for Accession AW368420, Feb. 6, 2000 (XP-002166666).
Nucleotide and Protein Database Report for Accession AJ251364.1, Oct. 16, 2000 (XP-002166667).
Nucleotide and Protein Database Report for Accession AJ251832, Oct. 25, 2000 (XP-002166668).

* cited by examiner

*Primary Examiner*—Kathleen M. Kerr
*Assistant Examiner*—Samuel W. Liu
(74) *Attorney, Agent, or Firm*—Alston & Bird LLP

(57) ABSTRACT

The present invention relates to identification of a gene upregulated by interferon-α administration corresponding to the cDNA sequence set forth in SEQ ID NO: 1. Determination of expression products of this gene is proposed as having utility in predicting responsiveness to treatment with interferon-a and other interferons which act at the Type 1 interferon receptor. Therapeutic use of the protein encoded by the same gene is also envisaged.

2 Claims, 2 Drawing Sheets

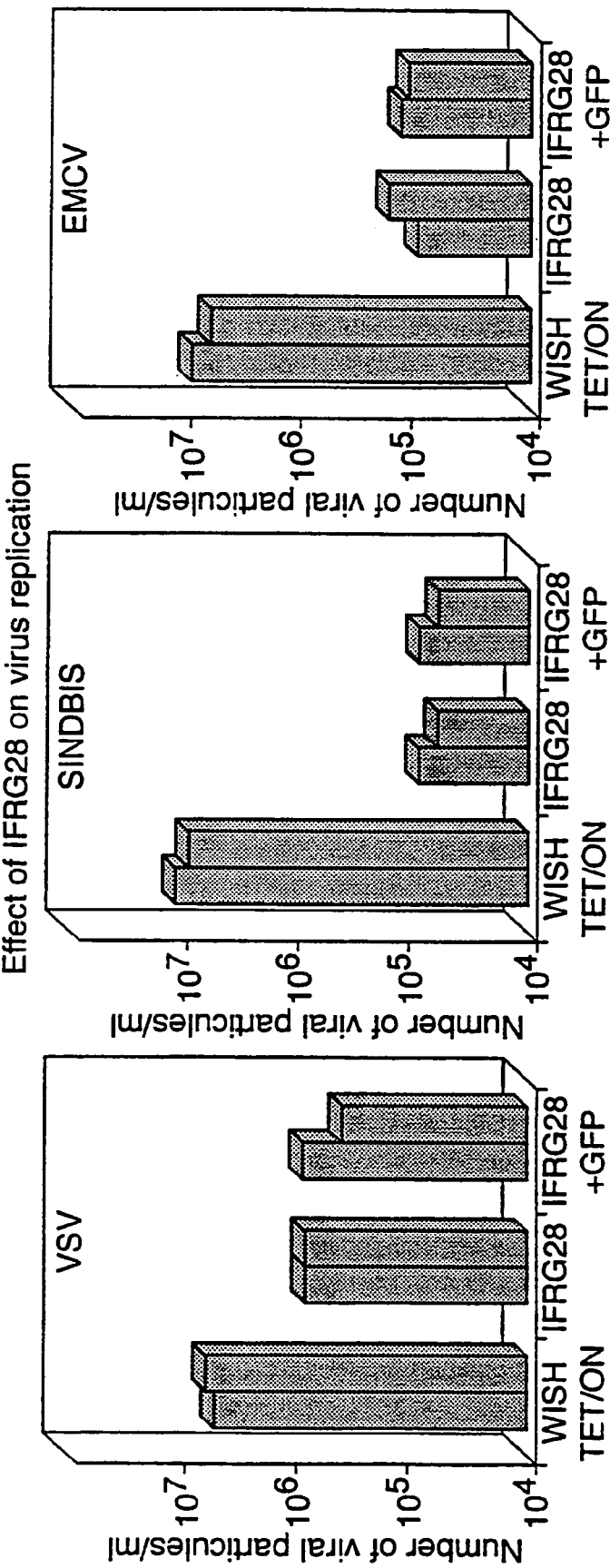

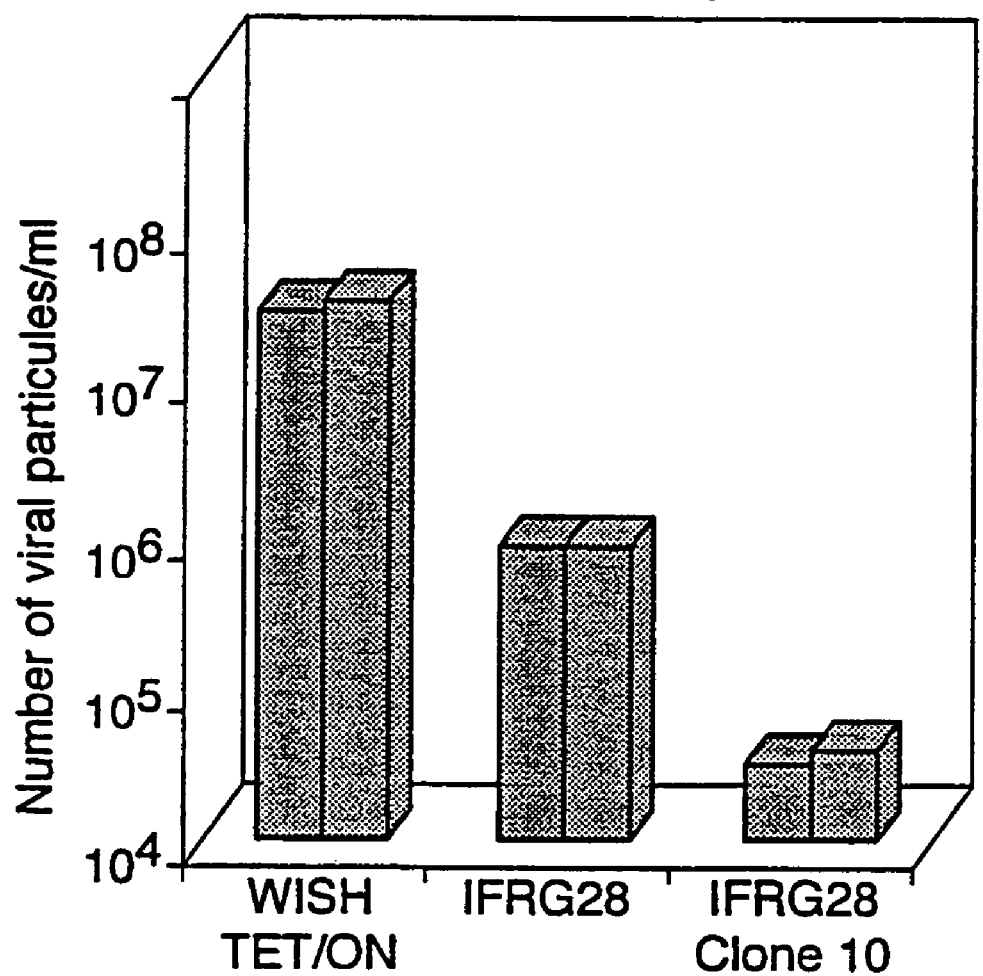

```
                        SEQUENCE LISTING

<160> NUMBER OF SEQ ID NOS: 2

<210> SEQ ID NO 1
<211> LENGTH: 1014
<212> TYPE: DNA
<213> ORGANISM: homo sapiens
<220> FEATURE:
<221> NAME/KEY: CDS
<222> LOCATION: (55)..(792)

<400> SEQUENCE: 1
ttcctcagaa acgagcaaac ctgaaagcta ctctctcagc ttcagaggga aaaa atg          57
                                                             Met
                                                             1 gtt gta gat ttc tgg act tgg gag cag aca ttt caa gaa cta atc caa        105
Val Val Asp Phe Trp Thr Trp Glu Gln Thr Phe Gln Glu Leu Ile Gln
        5                   10                  15 gag gca aaa ccc cgg gcc aca tgg acg ctg aag ttg gat ggc aac ctt        153
Glu Ala Lys Pro Arg Ala Thr Trp Thr Leu Lys Leu Asp Gly Asn Leu
 20                  25                  30 cag cta gac tgc ctg gct caa ggg tgg aag caa tac caa cag aga gca        201
Gln Leu Asp Cys Leu Ala Gln Gly Trp Lys Gln Tyr Gln Gln Arg Ala
     35                  40                  45 ttt ggc tgg ttc cgg tgt tcc tcc tgc cag cga agt tgg gct tcc gcc        249
Phe Gly Trp Phe Arg Cys Ser Ser Cys Gln Arg Ser Trp Ala Ser Ala
 50                  55                  60                  65 aag ttg cag att ctg tgc cac acg tac tgg gag cac tgg aca tcc cag        297
Lys Leu Gln Ile Leu Cys His Thr Tyr Trp Glu His Trp Thr Ser Gln
                 70                  75                  80 ggt cag gtg cgt atg agg ctc ttt ggc caa agg tgc cag aag tgc tcc        345
Gly Gln Val Arg Met Arg Leu Phe Gly Gln Arg Cys Gln Lys Cys Ser
             85                  90                  95 tgg tcc caa tat gag atg cct gag ttc tcc tcg gat agc acc atg agg        393
Trp Ser Gln Tyr Glu Met Pro Glu Phe Ser Ser Asp Ser Thr Met Arg
         100                 105                 110
```

```
att ctg agc aac ctg gtg cag cat ata ctg aag aaa tac tat gga aat      441
Ile Leu Ser Asn Leu Val Gln His Ile Leu Lys Lys Tyr Tyr Gly Asn
    115                 120                 125 ggc atg agg aag tct cca gaa atg cca gta atc ctg gaa gtg tcc ctg      489
Gly Met Arg Lys Ser Pro Glu Met Pro Val Ile Leu Glu Val Ser Leu
130                 135                 140                 145 gaa gga tcc cat gac aca gcc aat tgt gag gca tgc act ttg ggc ata      537
Glu Gly Ser His Asp Thr Ala Asn Cys Glu Ala Cys Thr Leu Gly Ile
                150                 155                 160 tgt gga cag ggc tta aaa agc tac atg aca aag ccg tcc aaa tcc cta      585
Cys Gly Gln Gly Leu Lys Ser Tyr Met Thr Lys Pro Ser Lys Ser Leu
            165                 170                 175 ctc ccc cac cta aag act ggg aat tcc tca cct gga att ggt gct gtg      633
Leu Pro His Leu Lys Thr Gly Asn Ser Ser Pro Gly Ile Gly Ala Val
        180                 185                 190 tac ctc gca aac caa gcc aag aac cag tca gat gag gca aaa gag gct      681
Tyr Leu Ala Asn Gln Ala Lys Asn Gln Ser Asp Glu Ala Lys Glu Ala
    195                 200                 205 aag ggg agt ggg tat gag aaa tta ggg ccc agt cga gac cca gat cca      729
Lys Gly Ser Gly Tyr Glu Lys Leu Gly Pro Ser Arg Asp Pro Asp Pro
210                 215                 220                 225 ctg aac atc tgt gtc ttt att ttg ctg ctt gta ttt att gta gtc aaa      777
Leu Asn Ile Cys Val Phe Ile Leu Leu Leu Val Phe Ile Val Val Lys
                230                 235                 240 tgc ttt aca tca gaa tgatgaaaat aggcttgcca ctttctctta ttttaattcc      832
Cys Phe Thr Ser Glu
            245
atggtagtca atgaactggc tgccacttta atataactga aaattcattt tgagaccaag    892
caggatcaag tttgtagaat aaacactggt ttcctagcta tcctctgaaa acagtatgaa    952
acatgaccaa gtacataatg gatttagtaa taaatattgt cgaattgcta aaaaaaaaaa   1012
aa                                                                  1014

<210> SEQ ID NO 2
<211> LENGTH: 246
<212> TYPE: PRT
<213> ORGANISM: homo sapiens

<400> SEQUENCE: 2

Met Val Val Asp Phe Trp Thr Trp Glu Gln Thr Phe Gln Glu Leu Ile
1               5                   10                  15

Gln Glu Ala Lys Pro Arg Ala Thr Trp Thr Leu Lys Leu Asp Gly Asn
            20                  25                  30

Leu Gln Leu Asp Cys Leu Ala Gln Gly Trp Lys Gln Tyr Gln Gln Arg
        35                  40                  45

Ala Phe Gly Trp Phe Arg Cys Ser Ser Cys Gln Arg Ser Trp Ala Ser
    50                  55                  60

Ala Lys Leu Gln Ile Leu Cys His Thr Tyr Trp Glu His Trp Thr Ser
65                  70                  75                  80

Gln Gly Gln Val Arg Met Arg Leu Phe Gly Gln Arg Cys Gln Lys Cys
                85                  90                  95

Ser Trp Ser Gln Tyr Glu Met Pro Glu Phe Ser Ser Asp Ser Thr Met
            100                 105                 110

Arg Ile Leu Ser Asn Leu Val Gln His Ile Leu Lys Lys Tyr Tyr Gly
        115                 120                 125

Asn Gly Met Arg Lys Ser Pro Glu Met Pro Val Ile Leu Glu Val Ser
    130                 135                 140

Leu Glu Gly Ser His Asp Thr Ala Asn Cys Glu Ala Cys Thr Leu Gly
```

-continued

```
145                 150                 155                 160
Ile Cys Gly Gln Gly Leu Lys Ser Tyr Met Thr Lys Pro Ser Lys Ser
                165                 170                 175

Leu Leu Pro His Leu Lys Thr Gly Asn Ser Ser Pro Gly Ile Gly Ala
            180                 185                 190

Val Tyr Leu Ala Asn Gln Ala Lys Asn Gln Ser Asp Glu Ala Lys Glu
        195                 200                 205

Ala Lys Gly Ser Gly Tyr Glu Lys Leu Gly Pro Ser Arg Asp Pro Asp
    210                 215                 220

Pro Leu Asn Ile Cys Val Phe Ile Leu Leu Leu Val Phe Ile Val Val
225                 230                 235                 240

Lys Cys Phe Thr Ser Glu
                245
```

INTERFERON ALPHA RESPONSIVE PROTEIN

FIELD OF THE INVENTION

The present invention relates to identification of a human gene upregulated by interferon-α (IFN-α) administration, the coding sequence of which is believed to be previously unknown. Detection of expression products of this gene may find use in predicting responsiveness to IFN-α and other interferons which act at the Type 1 interferon receptor. Therapeutic use of the isolated novel protein encoded by the same gene is also envisaged.

BACKGROUND OF THE INVENTION

IFN-α is widely used for the treatment of a number of disorders. Disorders which may be treated using IFN-α include neoplastic diseases such as leukemia, lymphomas, and solid tumours, acquired immunodeficiency syndrome (AIDS)-related Kaposi's sarcoma and viral infections such as chronic hepatitis. IFN-α has also been proposed for administration via the oromucosal route for the treatment of autoimmune, mycobacterial, neurodegenerative, parasitic and viral disease. In particular, IFN-α has been proposed, for example, for the treatment of multiple sclerosis, leprosy, tuberculosis, encephalitis, malaria, cervical cancer, genital herpes, hepatitis B and C, human immunodeficiency virus (HIV), human papillomavirus (HPV) and herpes simplex virus (HSV)-1 and 2. It has also been suggested for the treatment of arthritis, lupus and diabetes. Neoplastic diseases such as multiple myeloma, hairy cell leukemia, chronic myelogenous leukemia, low grade lymphoma, cutaneous T-cell lymphoma, carcinoid tumours, cervical cancer sarcomas including Kaposi's sarcoma, kidney tumours, carcinomas including renal cell carcinoma, hepatic cellular carcinoma, nasopharyngeal carcinoma, haematological malignancies, colorectal cancer, glioblastoma, laryngeal papillomas, lung cancer, colon cancer, malignant melanoma and brain tumours are also suggested as being treatable by administration of-IFN-α via the oromucosal route, i.e. the oral route or the nasal route.

IFN-α is a member of the Type 1 interferon family, which exert their characteristic biological activities through interaction with the Type 1 interferon receptor. Other Type 1 interferons include IFN-β, IFN-ω and IFN-τ.

Unfortunately, not all potential patients for treatment with a Type 1 interferon such as interferon-α, particularly, for example, patients suffering from chronic viral hepatitis, neoplastic disease and relapsing remitting multiple sclerosis, respond favourably to Type 1 interferon therapy and only a fraction of those who do respond exhibit long-term benefit. The inability of the physician to confidently predict the therapeutic outcome of Type 1 interferon treatment raises serious concerns as to the cost-benefit ratio of such treatment, not only in terms of wastage of an expensive biopharmaceutical and lost time in therapy, but also in terms of the serious side effects to which the patient is exposed. Furthermore, abnormal production of IFN-α has been shown to be associated with a number of autoimmune diseases. For these reasons, there is much interest in identifying Type 1 interferon responsive genes since Type 1 interferons exert their therapeutic action by modulating the expression of a number of genes. Indeed, it is the specific pattern of gene expression induced by Type 1 interferon treatment that determines whether a patient will respond favourably or not to the treatment.

SUMMARY OF THE INVENTION

A human gene cDNA has now been identified as corresponding to a mouse gene upregulated by administration of IFN-α by an oromucosal route or intravenously and is believed to represent a novel DNA. The corresponding human gene is thus now also designated an IFN-α upregulated gene.

The protein encoded by the same gene has a molecular weight of about 28 Kda and is referred to below as HuIFRG 28-1 protein. This protein, and functional variants thereof, are now envisaged as therapeutic agents, in particular for use as an anti-viral, anti-tumour or immunomodulatory agent. For example, they may be used in the treatment of autoimmune, mycobacterial, neurodegenerative, parasitic or viral disease, arthritis, diabetes, lupus, multiple sclerosis, leprosy, tuberculosis, encephalitis, malaria, cervical cancer, genital herpes, hepatitis B or C, HIV, HPV, HSV-1 or 2, or neoplastic disease such as multiple myeloma, hairy cell leukemia, chronic myelogenous leukemia, low grade lymphoma, cutaneous T-cell lymphoma, carcinoid tumours, cervical cancer, sarcomas including Kaposi's sarcoma, kidney tumours, carcinomas including renal cell carcinoma, hepatic cellular carcinoma, nasopharyngeal carcinoma, haematological malignancies, colorectal cancer, glioblastoma, laryngeal papillomas, lung cancer, colon cancer, malignant melanoma or brain tumours. In other words, such a protein may find use in treating any Type 1 interferon treatable disease.

Determination of the level of HuIFRG28-1 protein or a naturally-occurring variant thereof, or the corresponding mRNA, in cell samples of Type 1 interferon-treated patients, e.g. patients treated with IFN-α, e.g. such as by the oromucosal route or intravenously, may also be used to predict responsiveness to such treatment. It has additionally been found that alternatively, and more preferably, such responsiveness may be judged, for example, by treating a sample of human peripheral blood mononuclear cells in vitro with a Type 1 interferon and looking for upregulation or downregulation of an expression product, preferably mRNA, corresponding to the HuIFRG-28-1 gene.

According to a first aspect of the invention, there is thus provided an isolated polypeptide comprising:
  (i) the amino acid sequence of SEQ ID NO: 2;
  (ii) a variant thereof having substantially similar function. e.g. an immunomodulatory activity and/or an anti-viral activity and/or an anti-tumour activity; or
  (iii) a fragment of (i) or (ii) which retains substantially similar function, e.g. an immunomodulatory activity and/or an anti-viral activity and/or an anti-tumour activity.

The invention also provides such a protein for use in therapeutic treatment of a human or non-human animal, more particularly for use as an anti-viral, anti-tumour or immunomodulatory agent. As indicated above, such use may extend to any Type 1 interferon treatable disease.

According to another aspect of the invention, there is provided an isolated polynucleotide encoding a polypeptide of the invention as defined above or a complement thereof. Such a polynucleotide will typically include a sequence comprising:
  (a) the nucleic acid of SEQ ID NO: 1 or the coding sequence thereof and/or a sequence complementary thereto;
  (b) a sequence which hybridises, e.g. under stringent conditions, to a sequence complementary to a sequence as defined in (a);

(c) a sequence which is degenerate as a result of the genetic code to a sequence as defined in (a) or (b);
(d) a sequence having at least 60% identity to a sequence as defined in (a), (b) or (c).

The invention also provides;

an expression vector which comprises a polynucleotide of the invention and which is capable of expressing a polypeptide of the invention;

a host cell containing an expression vector of the invention;

an antibody specific for a polypeptide of the invention;

a method of treating a subject having a Type 1 interferon treatable disease, which method comprises administering to the said patient an effective amount of HuIFRG28-1 protein or a functional variant thereof use of such a polypeptide in the manufacture of a medicament for use in therapy as an anti-viral or anti-tumour or immunomodulatory agent, more particularly for use in treatment of a Type 1 interferon treatable disease;

a pharmaceutical composition comprising a polypeptide of the invention and a pharmaceutically acceptable carrier or diluent;

a method of producing a polypeptide of the invention, which method comprises maintaining host cells of the invention under conditions suitable for obtaining expression of the polypeptide and isolating the said polypeptide;

a polynucleotide of the invention. e.g. in the form of an expression vector, which directs expression in vivo of a polypeptide as defined above for use in therapeutic treatment of a human or non-human animal, more particularly for use as an anti-viral, anti-tumour or immunomodulatory agent;

a pharmaceutical composition comprising such a polynucleotide and a pharmaceutically acceptable carrier or diluent;

a method of treating a subject having a Type 1 interferon treatable disease, which method comprises administering to said patient an effective amount of such a polynucleotide;

use of such a polynucleotide in the manufacture of a medicament. e.g. a vector preparation, for use in therapy as an anti-viral, anti-tumour or immunomodulatory agent, more particularly for use in treating a Type 1 interferon treatable disease; and a method of identifying a compound having immunomodulatory activity and/or anti-viral activity and/or anti-tumour activity comprising providing a cell capable of expressing HuIFRG28-1 protein or a naturally occurring variant thereof, incubating said cell with a compound under test and monitoring for upregulation of HuIFRG28-1 gene expression.

In a still further aspect, the invention provides a method of predicting responsiveness of a patient to treatment with a Type 1 interferon. e.g. IFN-α treatment (such as IFN-α treatment by the oromucosal route or a parenteral route, for example, intravenously, subcutaneously, or intramuscularly), which comprises determining the level of HuIFRG28-1 protein or a naturally-occurring variant thereof, e.g. an allelic variant, or the corresponding mRNA, in a cell sample from said patient, e.g. a blood sample, wherein said sample is obtained from said patient following administration of a Type 1 interferon, e.g. IFN-α by an oromucosal route or intravenously, or is treated prior to said determining with a Type 1 interferon such as IFN-α in vitro. The invention also extends to kits for carrying out such testing.

DESCRIPTION OF THE FIGURES

FIG. 1 shows the effect of HuIFRG28-1 on viral replication of vesicular stomatitis virus (VSV), sindbis virus and encephalomyocarditis virus (EMCV).

FIG. 2 shows the effect of HuIFRG28 on viral replication of VSV.

BRIEF DESCRIPTION OF THE SEQUENCES

SEQ ID NO: 1 is the amino acid sequence of human protein HuIFRG28-1 and its encoding cDNA.

SEQ ID NO: 2 is the amino acid sequence alone of HuIFRG28-1 protein.

DETAILED DESCRIPTION OF THE INVENTION

As indicated above, human protein HuIFRG28-1 and functional variants thereof are now envisaged as therapeutically useful agents, more particularly for use as an anti-viral, anti-tumour or immunomodulatory agent.

A variant of HuIFRG28-1 protein for this purpose may be a naturally occurring variant, either an allelic variant or species variant, which has substantially the same functional activity as HuIFRG28-1 protein and is also upregulated in response to administration of IFN-α. Alternatively, a variant of HuIFRG28-1 protein for therapeutic use may comprise a sequence which varies from SEQ ID NO: 2 but which is a non-natural mutant.

The term "functional variant" refers to a polypeptide which has the same essential character or basic function of HuIFRG28-1 protein. The essential character of HuIFRG28-1 protein may be deemed to be as an immunomodulatory peptide. A functional variant polypeptide may show additionally or alternatively anti-viral activity and/or anti-tumour activity. In a preferred aspect, a variant or fragment demonstrates anti-viral activity.

Desired anti-viral activity may, for example, be tested as follows. A sequence encoding a variant to be tested is cloned into a retroviral vector such as a retroviral vector derived from the Moloney murine leukemia virus (MoMuLV) containing the viral packaging signal ψ, and a drug-resistance marker. A pantropic packaging cell line containing the viral gag, and pol, genes is then co-transfected with the recombinant retroviral vector and a plasmid, pVSV-G, containing the vesicular stomatitis virus envelope glycoprotein in order to produce high-titre infectious replication incompetent virus (Burns et al., Proc. Natl. Acad. Sci. USA 84, 5232–5236). The infectious recombinant virus is then used to transfect interferon sensitive fibroblasts or lymphoblastoid cells and cell lines that stably express the variant protein are then selected and tested for resistance to virus infection in a standard interferon bio-assay (Tovey et al., Nature, 271, 622–625, 1978). Growth inhibition using a standard proliferation assay (Mosmann, T., J. Immunol. Methods, 65, 55–63, 1983) and expression of MHC class I and class II antigens using standard techniques may also be determined.

A desired functional variant of HuIFRG28-1 may consist essentially of the sequence of SEQ ID NO: 2. A functional variant of SEQ ID NO: 2 may be a polypeptide which has a least 60% to 70% identity, preferably at least 80% or at least 90% and particularly preferably at least 95%, at least 97% or at least 99% identity with the amino acid sequence of SEQ ID NO: 2 over a region of at least 20, preferably at least 30, for instance at least 100 contiguous amino acids or over the full length of SEQ ID NO: 2. Methods of measuring protein identity are well known in the art.

Amino acid substitutions may be made, for example from 1, 2 or 3 to 10, 20 or 30 substitutions. Conservative substitutions may be made, for example according to the following Table. Amino acids in the same block in the second column and preferably in the same line in the third column may be substituted for each other.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Variant polypeptide sequences for therapeutic use in accordance with the invention may be shorter polypeptide sequences, for example, a peptide of at least 20 amino acids or up to 50, 60, 70, 80, 100, 150 or 200 amino acids in length is considered to fall within the scope of the invention provided it retains appropriate biological activity of HuIFRG28-1 protein. In particular, but not exclusively, this aspect of the invention encompasses the situation when the variant is a fragment of a complete natural naturally-occurring protein sequence.

Also encompassed by the invention are modified forms of HuIFRG28-1 protein and fragments thereof which can be used to raise anti-HuIFRG28-1 protein antibodies. Such variants will comprise an epitope of the HuIFRG28-1 protein.

Polypeptides of the invention may be chemically modified, e.g. post-translationally modified. For example, they may be glycosylated and/or comprise modified amino acid residues. They may also be modified by the addition of a sequence at the N-terminus and/or C-terminus, for example by provision of histidine residues or a T7 tag to assist their purification or by the addition of a signal sequence to promote insertion into the cell membrane. Such modified polypeptides fall within the scope of the term "polypeptide" of the invention.

A polypeptide of the invention may be labelled with a revealing label. The revealing label may be any suitable label which allows the polypeptide to be detected. Suitable labels include radioisotopes such as $^{125}$I, $^{35}$S or enzymes, antibodies, polynucleotides and linkers such as biotin. Labelled polypeptides of the invention may be used in assays. In such assays it may be preferred to provide the polypeptide attached to a solid support. The present invention also relates to such labelled and/or immobilised polypeptides packaged in the form of a kit in a container. The kit may optionally contain other suitable reagent(s), control(s) or instructions and the like.

The polypeptides of the invention may be made synthetically or by recombinant means. Such polypeptides of the invention may be modified to include non-naturally occurring amino acids, e.g. D-amino acids. Variant polypeptides of the invention may have modifications to increase stability in vitro and/or in vivo. When the polypeptides are produced by synthetic means, such modifications may be introduced during production. The polypeptides may also be modified following either synthetic or recombinant production.

A number of side chain modifications are known in the protein modification art and may be present in polypeptides of the invention. Such modifications include, for example, modifications of amino acids by reductive alkylation by reaction with an aldehyde followed by reduction with NaBH$_4$, amidination with methylacetimidate or acylation with acetic anhydride.

Polypeptides of the invention will be in substantially isolated form. It will be understood that the polypeptides may be mixed with carriers or diluents which will not interfere with the intended purpose of the polypeptide and still be regarded as substantially isolated. A polypeptide of the invention may also be in substantially purified form, in which case it will generally comprise the polypeptide in a preparation in which more than 90%, for example more than 95%, 98% or 99%, by weight of polypeptide in the preparation is a polypeptide of the invention.

Polynucleotides

The invention also includes isolated nucleotide sequences that encode HuIFRG28-1 protein or a variant thereof as well as isolated nucleotide sequences which are complementary thereto. The nucleotide sequence may be DNA or RNA, single or double stranded, including genomic DNA, synthetic DNA or cDNA. Preferably the nucleotide sequence is a DNA sequence and most preferably, a cDNA sequence.

As indicated above, such a polynucleotide will typically include a sequence comprising:
  (a) the nucleic acid of SEO ID NO: 1 or the coding sequence thereof and/or a sequence complementary thereto;
  (b) a sequence which hybridises, e.g. under stringent conditions, to a sequence complementary to a sequence as defined in (a);
  (c) a sequence which is degenerate as a result of the genetic code to a sequence as defined in (a) or (b);
  (d) a sequence having at least 60% identity to a sequence as defined in (a), (b) or (c).

Polynucleotides comprising an appropriate coding sequence can be isolated from human cells or synthesised according to methods well known in the art, as described by way of example in Sambrook et al. (1989) Molecular Cloning: A Laboratory Manual, 2$^{nd}$ edition, Cold Spring Harbor Laboratory Press.

Polynucleotides of the invention may include within them synthetic or modified nucleotides. A number of different types of modification to polynucleotides are known in the art. These include methylphosphonate and phosphothioate backbones, addition of acridine or polylysine chains at the 3' and/or 5' ends of the molecule. Such modifications may be carried out in order to enhance the in vivo activity or lifespan of polynucleotides of the invention.

Typically a polynucleotide of the invention will include a sequence of nucleotides, which may preferably be a contiguous sequence of nucleotides, which is capable of hybridising under selective conditions to the coding sequence or the complement of the coding sequence of SEQ ID NO: 1. Such hybridisation will occur at a level significantly above background. Background hybridisation may occur, for example, because of other cDNAs present in a cDNA library. The signal level generated by the interaction between a polynucleotide of the invention and the coding sequence or complement of the coding sequence of SEQ ID NO: 1 will typically be at least 10 fold, preferably at least 100 fold, as intense as interactions between other polynucleotides and the coding sequence of SEQ ID NO: 1. The intensity of interaction may be measured, for example, by radiolabelling the probe, e.g. with $^{32}$P Selective hybridisation may typically be achieved using conditions of low stringency (0.3M sodium chloride and 0.03M sodium citrate at about 40° C.), medium stringency (for example, 0.3M sodium chloride and 0.03M sodium citrate at about 50° C.) or high stringency (for example, 0.03M sodium chloride and 0.003M sodium citrate at about 60° C.).

The coding sequence of SEQ ID No: 1 may be modified by nucleotide substitutions, for example from 1, 2 or 3 to 10, 25, 50 or 100 substitutions. Degenerate substitutions may be made and/or substitutions may be made which would result in a conservative amino acid substitution when the modified sequence is translated, for example as shown in the table above. The coding sequence of SEQ. ID. NO: 1 may alternatively or additionally be modified by one or more insertions and/or deletions and/or by an extension at either or both ends.

A polynucleotide of the invention capable of selectively hybridising to a DNA sequence selected from SEQ. ID No.1, the coding sequence thereof and DNA sequences complementary thereto will be generally at least 70%, preferably at least 80 or 90% and more preferably at least 95% or 97%, homologous to the target sequence. This homology may typically be over a region of at least 20, preferably at least 30, for instance at least 40, 60 or 100 or more contiguous nucleotides.

Any combination of the above mentioned degrees of homology and minimum sized may be used to define polynucleotides of the invention, with the more stringent combinations (i.e. higher homology over longer lengths) being preferred. Thus for example a polynucleotide which is at least 80% homologous over 25, preferably over 30 nucleotides forms may be found suitable, as may be a polynucleotide which is at least 90% homologous over 40 nucleotides.

Homologues of polynucleotide or protein sequences as referred to herein may be determined in accordance with well-known means of homology calculation, e.g. protein homology may be calculated on the basis of amino acid identity (sometimes referred to as "hard homology"). For example the UWGCG Package provides the BESTFIT program which can be used to calculate homology, for example used on its default settings, (Devereux et al. (1984) Nucleic Acids Research 12, 387–395). The PILEUP and BLAST algorithms can be used to calculate homology or line up sequences or to identify equivalent or corresponding sequences, typically used on their default settings, for example as described in Altschul S. F. (1993) J. Mol. Evol. 36, 290–300; Altschul, S. F. et al. (1990) J. Mol. Biol. 215, 403-10.

Software for performing BLAST analyses is publicly available through the National Center for Biotechnology Information (www.ncbi.nlm.nih.gov./). This algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value, the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Nati. Acad. Sci. USA 89, 10915–10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873–5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Polynucleotides according to the invention have utility in production of the proteins according to the invention, which may take place in vitro, in vivo or ex vivo. In such a polynucleotide, the coding sequence for the desired protein of the invention will be operably-linked to a promoter sequence which is capable of directing expression of the desired protein in the chosen host cell. Such a polynucleotide will generally be in the form of an expression vector. Polynucleotides of the invention, e.g. in the form of an expression vector, which direct expression in vivo of a polypeptide of the invention having immunomodulatory activity and/or anti-viral activity and/or anti-tumour activity may also be used as a therapeutic agent.

Expression vectors for such purposes may be constructed in accordance with conventional practices in the art of recombinant DNA technology. They may, for example, involve the use of plasmid DNA. They may be provided with an origin of replication. Such a vector may contain one or more selectable markers genes, for example an ampicillin resistance gene in the case of a bacterial plasmid. Other features of vectors of the invention may include appropriate initiators, enhancers and other elements, such as for example polyadenylation signals which may be desirable, and which are positioned in the correct orientation, in order to allow for protein expression. Other suitable non-plasmid vectors would be apparent to persons skilled in the art. By way of further example in this regard reference is made again to Sambrook et al. 1989 (supra). Such vectors additionally include, for example, viral vectors. Examples of suitable viral vectors include herpes simplex viral vectors, replication-defective retroviruses, including lentiviruses, adenoviruses, adeno-associated virus, HPV viruses (such as HPV-16 and HPV-18) and attenuated influenza virus vectors.

Promoters and other expression regulation signals may be selected to be compatible with the host cell for which expression is designed. For example, yeast promoters include *S. cerevisiae* GAL4 and ADH promoters, *S. pombe* nmt1 and adh promoter. Mammalian promoters include the metallothionein promoter which can be induced in response to heavy metals such as cadmium and β-actin promoters. Viral promoters such as the SV40 large T antigen promoter or adenovirus promoters may also be used. Other examples of viral promoters which may be employed include the Moloney murine leukemia virus long terminal repeat (MMLV LTR), the rous sarcoma virus (RSV) LTR promoter, the human cytomegalovirus (CMV) IE promoter, and HPV promoters, particularly the HPV upstream regulatory region (URR). Other suitable promoters will be well-known to those skilled in the recombinant DNA art.

An expression vector of the invention may further include sequences flanking the coding sequence for the desired polypeptide of the invention providing sequences homologous to eukaryotic genomic sequences, preferably mammalian genomic sequences, or viral genomic sequences. This will allow the introduction of such polynucleotides of the invention into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell.

The invention also includes cells in vitro, for example prokaryotic or eukaryotic cells, which have been modified to express the HuIFRG28-1 protein or a variant thereof. Such cells include stable, e.g. eukaryotic, cell lines wherein a polynucleotide encoding HuIFRG28-1 protein or a variant thereof is incorporated into the host genome. Host cells of the invention may be mammalian cells or insect cells, lower eukaryotic cells, such as yeast or prokaryotic cells such as bacterial cells. Particular examples of cells which may be modified by insertion of vectors encoding for a polypeptide according to the invention include mammalian HEK293T, CHO, HeLa and COS cells. Preferably a cell line may be chosen which is not only stable, but also allows for mature glycosylation of a polypeptide. Expression may, for example, be achieved in transformed oocytes.

A polypeptide of the invention may be expressed in cells of a transgenic non-human animal, preferably a mouse. A transgenic non-human animal capable of expressing a polypeptide of the invention is included within the scope of the invention.

Polynucleotides according to the invention may also be inserted into vectors as described above in an antisense orientation in order to provide for the production of antisense sequences. Antisense RNA or other antisense polynucleotides may also be produced by synthetic means.

A polynucleotide, e.g. in the form of an expression vector, capable of expressing in vivo an antisense sequence to a coding sequence for the amino acid sequence defined by SEQ ID NO: 1, or a naturally-occurring variant thereof, for use in therapeutic treatment of a human or non-human animal is also envisaged as constituting an additional aspect of the invention. Such a polynucleotide will find use in treatment of diseases associated with upregulation of HuIRG28-1 protein.

Polynucleotides of the invention extend to sets of primers for nucleic acid amplification which target sequences within the cDNA for a polypeptide of the invention, e.g. pairs of primers for PCR amplification. The invention also provides probes suitable for targeting a sequence within a cDNA or RNA for a polypeptide of the invention which may be labelled with a revealing label, e.g. a radioactive label or a non-radioactive label such as an enzyme or biotin. Such probes may be attached to a solid support. Such a solid support may be a micro-array (also commonly referred to as nucleic acid, probe or DNA chip) carrying probes for further nucleic acids. e.g. mRNAs or amplification products thereof corresponding to other Type 1 interferon upregulated genes. e.g. such genes identified as upregulated in response to oromucosal or intravenous administration of IFN-α. Methods for constructing such micro-arrays are well-known (see, for example, EP-B 0476014 and 0619321 of Affymax Technologies N.V. and Nature Genetics Supplement January 1999 entitled "The Chipping Forecast").

The nucleic acid sequence of such a primer or probe will preferably be at least 10, preferably at least 15 or at least 20, for example at least 25, at least 30 or at least 40 nucleotides in length. It may, however, be up to 40, 50, 60, 70, 100 or 150 nucleotides in length or even longer.

Another aspect of the invention is the use of probes or primers of the invention to identify mutations in HuIFRG28-1 genes, for example single nucleotide polymorphisms (SNPs).

As indicated above, in a still further aspect the present invention provides a method of identifying a compound having immunomodulatory activity and/or antiviral activity and/or anti-tumour activity comprising providing a cell capable of expressing HuIFRG28-1 protein or a naturally-occurring variant thereof, incubating said cell with a compound under test and monitoring for upregulation of HuIFRG28-1 gene expression. Such monitoring may be by probing for mRNA encoding HuIFRG28-1 protein or a naturally-occurring variant thereof. Alternatively antibodies or antibody fragments capable of specifically binding one or more of HuIFRG28-1 and naturally-occurring variants thereof may be employed.

Antibodies

According to another aspect, the present invention also relates to antibodies (for example polyclonal or preferably monoclonal antibodies, chimeric antibodies, humanised antibodies and fragments thereof which retain antigen-binding capability) which have been obtained by conventional techniques and are specific for a polypeptide of the invention. Such antibodies could, for example, be useful in purification, isolation or screening methods involving immunoprecipitation and may be used as tools to further elucidate the function or HuIFRG28-1 protein or a variant thereof. They may be therapeutic agents in their own right. Such antibodies may be raised against specific epitopes of proteins according to the invention. An antibody specifically binds to a protein when it binds with high affinity to the protein for which it is specific but does not bind or binds with only low affinity to other proteins. A variety of protocols for competitive binding or immunoradiometric assays to determine the specific binding capability of an antibody are well-known.

Pharmaceutical Compositions

A polypeptide of the invention is typically formulated for administration with a pharmaceutically acceptable carrier or diluent. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants. e.g. silica, talc, stearic acid, magnesium or calcium stearate, and/or polyethylene glycols; binding agents; e.g. starches, arabic gums, gelatin, methyl cellulose, carboxymethylcellulose or polyvinyl pyrrolidone; desegregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tableting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methyl cellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusions may contain as carrier, for example, sterile water or preferably they may be in the form of sterile, aqueous, isotonic saline solutions.

A suitable dose of HuIFRG28-1 protein or a functional analogue thereof for use in accordance with the invention may be determined according to various parameters, especially according to the substance used: the age, weight and condition of the patient to be treated; the route of administration; and the required regimen. Again, a physician will be able to determine the required route of administration and dosage for any particular patient. A typical daily dose may be from about 0.1 to 50 mg per kg, preferably from about 0.1 mg/kg to 10 mg/kg of body weight, according to the activity of the specific inhibitor, the age, weight and condition of the subject to be treated, and the frequency and route of administration. Preferably, daily dosage levels may be from 5 mg to 2 g.

A polynucleotide of the invention suitable for therapeutic use will also typically be formulated for administration with a pharmaceutically acceptable carrier or diluent. Such a polynucleotide may be administered by any known technique whereby expression of the desired polypeptide can be attained in vivo. For example, the polynucleotide may be introduced by injection, preferably intradermally, subcutaneously or intramuscularly. Alternatively, the nucleic acid may be delivered directly across the skin using a particle-mediated delivery device. A polynucleotide of the invention suitable for therapeutic nucleic acid may alternatively be administered to the oromucosal surface for example by intranasal or oral administration.

A non-viral vector of the invention suitable for therapeutic use may, for example, be packaged into liposomes or into surfactant containing vector delivery particles. Uptake of nucleic acid constructs of the invention may be enhanced by several known transfection techniques, for example those including the use of transfection agents. Examples of these agents include cationic agents, for example calcium phosphate and DEAE dextran and lipofectants, for example lipofectam and transfectam. The dosage of the nucleic acid to be administered can be varied. Typically, the nucleic acid will be administered in the range of from 1 pg to 1 mg, preferably from 1 pg to 10 μg nucleic acid for particle-mediated gene delivery and from 10 μg to 1 mg for other routes.

Polypeptides and polynucleotides of the invention may be used in therapy for the treatment of viral infection, tumours or as an immunomodulatory agent and for treating a Type 1 interferon treatable disease. In a preferred aspect, the polypeptides and polynucleotides are used in the treatment of viral infection, such as DNA or RNA viruses, and preferably RNA viruses.

Examples of conditions in which the polynucleotides and polypeptides of the invention may be useful include treatment of autoimmune, mycobacterial, neurodegenerative and parasitic disease, arthritis, diabetes, lupus multiple sclerosis, leprosy, tuberculosis, encephalitis, malaria, cervical cancer, genital herpes, hepatitis B and C, HIV, HPV and HSV-1 and 2, or neoplastic diseases such as multiple myeloma, hairy cell leukemia, chronic myelogenous leukemia, low grade lymphoma, cutaneous T-cell lymphoma, carcinoid tumours, cervical cancer, sarcomas including Kaposi's sarcoma, kidney tumours, carcinomas including renal cell carcinoma, hepatic cellular carcinoma, nasopharyngeal carcinoma haematological malignancies, colorectal cancer, glioblastoma, laryngeal papillomas, lung cancer, colon cancer, malignant melanoma and brain tumours.

Prediction of Type 1 Interferon Responsiveness

As also indicated above, in a still further aspect the present invention provides a method of predicting responsiveness of a patient to treatment with a Type 1 interferon, e.g. IFN-α treatment such as IFN-α treatment by an oromucosal route or intravenously, which comprises determining the level of HuIFRG28-1 protein or a naturally-occurring variant thereof, or the corresponding mRNA, in a cell sample from said patient, wherein said sample is taken from said patient following administration of a Type 1 interferon or is treated prior to said determining with a Type 1 interferon in vitro.

Preferably, the Type 1 interferon for testing responsiveness will be the Type 1 interferon selected for treatment. It may be administered by the proposed treatment route and at the proposed treatment dose. Preferably, the subsequent sample analysed may be, for example, a blood sample or a sample of peripheral blood mononuclear cells (PBMCs) isolated from a blood sample.

More conveniently and preferably, a sample obtained from the patient comprising PBMCs isolated from blood may be treated in vitro with a Type 1 interferon, e.g. at a dosage range of about 1 to 10,000 IU/ml. Such treatment may be for a period of hours. e.g. about 7 to 8 hours. Preferred treatment conditions for such in vitro testing may be determined by testing PBMCs taken from normal donors with the same interferon and looking for upregulation of an appropriate expression product. Again, the Type 1 interferon employed will preferably be the Type 1 interferon proposed for treatment of the patient, e.g. recombinant IFN-α. PBMCs for such testing may be isolated in conventional manner from a blood sample using Ficoll-Hypaque density gradients. An example of a suitable protocol for such in vitro testing of Type 1 interferon responsiveness is provided in Example 3 below.

The sample, if appropriate after in vitro treatment with a Type 1 interferon, may be analysed for the level of HuIFRG28-1 protein or a naturally-occurring variant thereof. This may be done using an antibody or antibodies capable of specifically binding one or more of HuIFRG28-1 protein and naturally-occurring variants thereof. e.g. allelic variants thereof. Preferably, however, the sample will be analysed for mRNA encoding HuIFRG28-1 protein or a naturally-occurring variant thereof. Such mRNA analysis may employ any of the techniques known for detection of mRNAs, e.g. Northern blot detection or mRNA differential display. A variety of known nucleic acid amplification protocols may be employed to amplify any mRNA of interest present in the sample, or a portion thereof, prior to detection. The mRNA of interest, or a corresponding amplified nucleic acid, may be probed for using a nucleic acid probe attached to a solid support. Such a solid support may be a micro-array as previously discussed above carrying probes to determine the level of further mRNAs or amplification products thereof corresponding to Type 1 interferon upregulated genes, e.g. such genes identified as upregulated in response to oromucosal or intravenous administration of IFN-α.

The following examples illustrate the invention:

EXAMPLES

Example 1

Previous experiments had shown that the application of 5 µl of crystal violet to each nostril of a normal adult mouse using a P20 Eppendorf micropipette resulted in an almost immediate distribution of the dye over the whole surface of the oropharyngeal cavity. Staining of the oropharyngeal cavity was still apparent some 30 minutes after application of the dye. These results were confirmed by using $^{125}$I-labelled recombinant human IFN-α1–8 applied in the same manner. The same method of administration was employed to effect oromucosal administration in the studies which are described below.

Six week old, male DBA/2 mice were treated with either 100,000 IU of recombinant murine interferon α (IFN α) purchased from Life Technologies Inc. in phosphate buffered saline (PBS), 10 µg of recombinant human interleukin 15 (IL-15) purchased from Protein Institute Inc, PBS containing 100 µg/ml of bovine serum albumin (BSA), or left untreated. Eight hours later, the mice were sacrificed by cervical dislocation and the lymphoid tissue was removed surgically from the oropharyngeal cavity and snap frozen in liquid nitrogen and stored at −80° C. RNA was extracted from the lymphoid tissue by the method of Chomczynski and Sacchi 1987. (Anal. Biochem. 162, 156–159) and subjected to mRNA Differential Display Analysis (Lang, P. and Pardee, A. B., Science, 257, 967–971).

Differential Display Analysis

Differential display analysis was carried out using the "Message Clean" and "RNA image" kits of the GenHunter Corporation essentially as described by the manufacturer. Briefly, RNA was treated with RNase-free DNase, and 1 µg was reverse-transcribed in 100 µl of reaction buffer using either one or the other of the three one-base anchored oligo-(dT) primers A, C, or G. RNA was also reverse-transcribed using one or the other of the 9 two-base anchored oligo-(dT) primers AA, CC, GG, AC, CA, GA, AG, CG, GC. All the samples to be compared were reverse transcribed in the same experiment, separated into aliquots and frozen. The amplification was performed with only 1 µl of the reverse transcription sample in 10 µl of amplification mixture containing Taq DNA polymerase and α-$^{33}$P dATP (3,000 Ci/mmole). Eighty 5' end (HAP) random sequence primers were used in combination with each of the (HT11) A, C, G, AA, CC, GG, AC, CA, GA, AG, CG or GC primers. Samples were then run on 7% denaturing polyacrylamide gels and exposed to authoradiography. Putative differentially expressed bands were cut out, reamplified according to the instructions of the supplier, and further used as probes to hybridize Northern blots of RNA extracted from the oropharyngeal cavity of IFN treated, IL-15 treated, and excipient treated animals.

Cloning and Sequencing

Re-amplified bands from the differential display screen were cloned in the Sfr 1 site of the pPCR-Script SK(+) plasmid (Stratagene) and cDNAs amplified from the rapid amplification of cDNA ends were isolated by TA cloning in the pCR3 plasmid (Invitrogen). DNA was sequenced using an automatic di-deoxy sequencer (Perkin Elmer ABI PRISM 377).

Isolation of Human cDNA

Differentially expressed murine 3' sequences identified from the differential display screen were compared with random human expressed, sequence tags (EST) present in the dbEST database of GenBank™ of the United States National Center for Biotechnology Information (NCBI). The sequences potentially related to the murine EST isolated from the differential display screen were combined in a contig and used to construct a human consensus sequence corresponding to a putative cDNA. One such cDNA was found to be 1014 nucleotides in length. This corresponded to a mouse gene whose expression was found to be enhanced approximately 3-fold in the lymphoid tissue of the oral cavity of mice following oromucosal administration of IFN-α.

In order to establish that this putative cDNA corresponded to an authentic human gene, primers derived from the 5' and 3' ends of the consensus sequence were used to synthesise cDNA from mRNA extracted from human peripheral blood leukocytes (PBL) by specific reverse transcription and PCR amplification. A unique cDNA fragment of the predicted size was obtained, cloned and sequenced (SEQ ID NO: 1). This human cDNA contains an open reading frame (ORF) of 741 bp in length at positions 55–795 encoding a protein of 246 amino acids (SEQ ID NO: 2).

Example 2

Intravenous Administration of IFN-α

Male DBA/2 mice were injected intravenously with 100,000 IU of recombinant murine IFN-α purchased from Life Technologies Inc. in 200 µl of PBS or treated with an equal volume of PBS alone. Eight hours later, the animals were sacrificed by cervical dislocation and the spleen was removed using conventional procedures. Total RNA was extracted by the method of Chomczynski and Sacchi (Anal. Biochem. (1987) 162, 156–159) and 10.0 µg of total RNA per sample was subjected to Northern blotting in the presence of glyoxal and hybridised with a cDNA probe for HuIFRG28-1 mRNA as described by Dandoy-Dron et al. (J. Biol. Chem. (1998) 273, 7691–7697). The blots were first exposed to autoradiography and then quantified using a PhosphoImager according to the manufacturer's instructions. Enhanced levels of mRNA for HuIFRG28-1 protein (approximately 5 to 10 fold) were detected in samples of RNA extracted from spleens of IFN-α treated animals relative to animals treated with excipient alone.

Example 3

Testing Type 1 Interferon Responsiveness in Vitro

Human peripheral blood mononuclear cells (PBMCs) from normal donors were isolated on Ficoll-Hypaque density gradients and treated in vitro with 10,000 IU of recombinant human IFN-α2 (Intron A from Schering-Plough) in PBS or with an equal volume of PBS alone. Eight hours later the cells were centrifuged (800×g for 10 minutes) and the cell pellet recovered. Total RNA was extracted from the cell pellet by the method of Chomczynski and Sacchi and 10.0 µg of total RNA per sample was subjected to Northern blotting in the presence of glyoxal and hybridised with a cDNA probe for HuIFRG28-1 mRNA as previously described in Example 2 above. Enhanced levels of mRNA for HUIFRG28-1 protein (approximately 10-fold) were detected in samples of RNA extracted from IFN-α treated PBMCs compared to samples treated with PBS alone.

The same procedure may be used to predict Type 1 interferon responsiveness using PBMCs taken from a patient proposed to be treated with a Type 1 interferon.

Example 4

Determination of the Antiviral Activity of HuIFRG 28-1

The HuIFRG 28-1 cDNA or a cDNA encoding the HuIFRG28-1-GFP fusion protein was subcloned into plasmid pRev-TRE which was then used to transfect the Amphopack encapsidation line (Clonetech) as described by the manufacturer. The cell supernatant containing the retroviral vector was then collected and used to serially infect the HeLa Tet/On or WISH Tet. On target cells (Clonetech) as described by the manufacturer. Two to three days after the last serial infection of the target cells with virus derived from the Amphopack cell line the target cells were treated with hygromycin and resistant clones were isolated by limiting dilution.

The effect of the expression of the native HuIFRG28-1 protein or the HuIFRG28-1-GFP fusion protein on the replication of three different RNA viruses was determined in clones of cells transfected with the gene encoding either the native HuIFRG28-1 protein or the HuIFRG28-1-GFP fusion protein in the presence or absence of doxycycline. The RNA viruses tested were: Encephalomyocarditis virus (EMCV) a Picornavius, Sindbis, the prototype Alphavirus, and Vesicular Stomatitis virus (VSV), a Rhabdovirus.

Briefly, cells treated for 24 hours in the presence or absence of 1.0 μg/ml of doxycycline were infected with a particular virus at a multiplicity of infection of 1.0. One hour later the virus inoculum was removed, the cells were washed three times, and incubated for 24 hours in growth medium at 37° C. The cells were then frozen and thawed 6 times at −80° C., cell debris was removed by centrifugation and the virus present in the supernatant was assayed as the mean of 8 separate determinations at each ten fold dilution ranging from $10^3$ to $10^{10}$ by detection of cytopathic effect on monkey CV1 Vero cells.

Expression of either the native HuIFRG28-1 protein or the HuIFRG28-1-GFP fusion protein was found to exhibit a marked antiviral activity against EMCV, VSV, and Sindbis virus in both the total cell population (FIG. 1) and in an individual clone (FIG. 2).

The invention claimed is:

1. An isolated polypeptide comprising:

(a) the amino acid sequence of SEQ ID NO: 2; or (b) a variant of (a) having at least 95% amino acid sequence identity over the full length of SEQ ID NO: 2 and having anti-viral activity against encephalomyocarditis virus (EMCV), Sindbis virus or Vesicular Stomatitis virus (VSV).

2. A pharmaceutical composition comprising a polypeptide and a pharmaceutically acceptable carrier or diluent, wherein the polypeptide comprises:

(a) the amino acid sequence of SEQ ID NO: 2; or (b) a variant of (a) having at least 95% amino acid sequence identity over the full length of SEQ ID NO: 2 and having anti-viral activity against encephalomyocarditis virus (EMCV), Sindbis virus or Vesicular Stomatitis virus (VSV).

* * * * *